(12) United States Patent
Anderson

(10) Patent No.: US 8,131,342 B2
(45) Date of Patent: Mar. 6, 2012

(54) METHOD AND SYSTEM FOR FIELD MAPPING USING INTEGRAL METHODOLOGY

(75) Inventor: Peter Traneus Anderson, Andover, MA (US)

(73) Assignee: General Electric Company, Schenectady, NY (US)

( * ) Notice: Subject to any disclaimer, the term of this patent is extended or adjusted under 35 U.S.C. 154(b) by 2325 days.

(21) Appl. No.: 10/925,238

(22) Filed: Aug. 24, 2004

(65) Prior Publication Data

US 2006/0055712 A1    Mar. 16, 2006

(51) Int. Cl.
*A61B 5/05* (2006.01)
*G01S 1/02* (2010.01)

(52) U.S. Cl. ............... 600/424; 324/207.12; 324/207.17

(58) Field of Classification Search .................. 600/407, 600/410–411, 414–415, 424, 426, 429, 437; 606/130; 702/150, 153, 75, 94–95; 324/318, 324/207.12–207.14, 244
See application file for complete search history.

(56) References Cited

U.S. PATENT DOCUMENTS

| | | | |
|---|---|---|---|
| 3,868,565 A | 2/1975 | Kuipers | |
| 3,983,474 A | 9/1976 | Kuipers | |
| 4,054,881 A * | 10/1977 | Raab | 342/448 |
| 4,176,662 A | 12/1979 | Frazier | |
| 4,613,866 A | 9/1986 | Blood | |
| 4,618,822 A | 10/1986 | Hansen | |
| 4,622,644 A * | 11/1986 | Hansen | 702/153 |
| 4,642,786 A | 2/1987 | Hansen | |
| 4,710,708 A | 12/1987 | Rorden et al. | |
| 4,737,794 A | 4/1988 | Jones | |
| 4,742,356 A | 5/1988 | Kuipers | |
| 5,099,845 A | 3/1992 | Besz et al. | |
| 5,143,688 A * | 9/1992 | Mansfield | 324/318 |
| 5,211,165 A | 5/1993 | Dumoulin et al. | |
| 5,251,635 A | 10/1993 | Dumoulin et al. | |
| 5,255,680 A | 10/1993 | Darrow | |
| 5,265,610 A | 11/1993 | Darrow | |
| 5,307,072 A | 4/1994 | Jones | |
| 5,377,678 A | 1/1995 | Dumoulin et al. | |
| 5,425,367 A | 6/1995 | Shapiro | |
| 5,425,382 A | 6/1995 | Golden et al. | |
| 5,437,277 A | 8/1995 | Dumoulin | |
| 5,443,066 A | 8/1995 | Dumoulin et al. | |

(Continued)

OTHER PUBLICATIONS

Peter T. Anderson, A Source of Accurately Calculable Quasi-Static Magnetic Fields, Oct. 2001.

(Continued)

*Primary Examiner* — Francis Jaworski
(74) *Attorney, Agent, or Firm* — McAndrews, Held & Malloy, Ltd.; William Baxter

(57) ABSTRACT

Certain embodiments of the present invention provide a system and method for improved distortion measurement and compensation. Certain embodiments include selecting a set of sources on a surface of a volume, determining mutual inductances from the set of sources on the surface, and calculating distortion from the volume using the mutual inductances from the set of sources on the surface. In an embodiment, distortion is calculated using an integral method and/or a finite element analysis. The volume may be modeled as a simplified construct, such as a ring model, a coil array with straight line segments model, a polygon model, and/or dipole array model. The model may be adjusted based on the distortion calculated from the volume. Magnetic fields may also be used to calculate distortion. In an embodiment, an object may be tracked using a distortion mapping.

18 Claims, 5 Drawing Sheets

U.S. PATENT DOCUMENTS

| | | | |
|---|---|---|---|
| 5,445,150 A | 8/1995 | Dumoulin et al. | |
| 5,488,566 A * | 1/1996 | Woolsey | 324/207.15 |
| 5,517,195 A | 5/1996 | Narlow et al. | |
| 5,557,247 A * | 9/1996 | Vaughn, Jr. | 333/219 |
| 5,558,091 A | 9/1996 | Acker | |
| 5,592,939 A | 1/1997 | Martinelli | |
| 5,622,169 A | 4/1997 | Golden et al. | |
| 5,847,976 A | 12/1998 | Lescourret | |
| 6,052,610 A | 4/2000 | Koch | |
| 6,073,043 A * | 6/2000 | Schneider | 600/424 |
| 6,129,667 A | 10/2000 | Dumoulin | |
| 6,129,668 A | 10/2000 | Haynor et al. | |
| 6,172,499 B1 * | 1/2001 | Ashe | 324/207.12 |
| 6,177,792 B1 * | 1/2001 | Govari et al. | 324/207.12 |
| 6,188,355 B1 | 2/2001 | Gilboa | |
| 6,201,987 B1 * | 3/2001 | Dumoulin | 600/424 |
| 6,226,547 B1 | 5/2001 | Lockhart | |
| 6,230,038 B1 | 5/2001 | von Gutfeld et al. | |
| 6,233,476 B1 * | 5/2001 | Strommer et al. | 600/424 |
| 6,236,875 B1 * | 5/2001 | Bucholz et al. | 600/407 |
| 6,259,372 B1 | 7/2001 | Taranowski et al. | |
| 6,369,564 B1 * | 4/2002 | Khalfin et al. | 324/207.17 |
| 6,374,131 B1 | 4/2002 | Tomita et al. | |
| 6,374,134 B1 * | 4/2002 | Bladen et al. | 600/424 |
| 6,377,041 B1 * | 4/2002 | Jones et al. | 324/244 |
| 6,400,139 B1 * | 6/2002 | Khalfin et al. | 324/207.17 |
| 6,427,079 B1 * | 7/2002 | Schneider et al. | 600/424 |
| 6,427,314 B1 * | 8/2002 | Acker | 29/593 |
| 6,459,882 B1 | 10/2002 | Palermo | |
| 6,463,039 B1 | 10/2002 | Ricci | |
| 6,472,975 B1 | 10/2002 | Beigel et al. | |
| 6,484,118 B1 * | 11/2002 | Govari | 702/150 |
| 6,499,488 B1 * | 12/2002 | Hunter et al. | 128/899 |
| 6,528,989 B1 * | 3/2003 | Hansen | 324/207.12 |
| 2002/0065461 A1 * | 5/2002 | Cosman | 600/426 |
| 2010/0056905 A1 * | 3/2010 | Anderson | 600/424 |

OTHER PUBLICATIONS

Tom Ahlkvist Scharfeld, An Analysis of the Fundamental Constraints on Low Cost Passive Radio-Frequency Identification System Design, Aug. 2001.

* cited by examiner

METHOD AND SYSTEM FOR FIELD MAPPING USING INTEGRAL METHODOLOGY

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to imaging and image-guided navigation. In particular, the present invention relates to a system and method for improved image-guided navigation by distortion mapping using integral methods.

Medical practitioners, such as doctors, surgeons, and other medical professionals, often rely upon technology when performing a medical procedure, such as image-guided surgery or examination. A tracking system may provide positioning information for the medical instrument with respect to the patient or a reference coordinate system, for example. A medical practitioner may refer to the tracking system to ascertain the position of the medical instrument when the instrument is not within the practitioner's line of sight. A tracking system may also aid in pre-surgical planning.

The tracking or navigation system allows the medical practitioner to visualize the patient's anatomy and track the position and orientation of the instrument. The medical practitioner may use the tracking system to determine when the instrument is positioned in a desired location. The medical practitioner may locate and operate on a desired or injured area while avoiding other structures. Increased precision in locating medical instruments within a patient may provide for a less invasive medical procedure by facilitating improved control over smaller instruments having less impact on the patient. Improved control and precision with smaller, more refined instruments may also reduce risks associated with more invasive procedures such as open surgery.

Tracking systems may also be used to track the position of items other than medical instruments in a variety of applications. That is, a tracking system may be used in other settings where the position of an instrument in an object or an environment is difficult to accurately determine by visual inspection. For example, tracking technology may be used in forensic or security applications. Retail stores may use tracking technology to prevent theft of merchandise. In such cases, a passive transponder may be located on the merchandise. A transmitter may be strategically located within the retail facility. The transmitter emits an excitation signal at a frequency that is designed to produce a response from a transponder. When merchandise carrying a transponder is located within the transmission range of the transmitter, the transponder produces a response signal that is detected by a receiver. The receiver then determines the location of the transponder based upon characteristics of the response signal.

Tracking systems are also often used in virtual reality systems or simulators. Tracking systems may be used to monitor the position of a person in a simulated environment. A transponder or transponders may be located on a person or object. A transmitter emits an excitation signal and a transponder produces a response signal. The response signal is detected by a receiver. The signal emitted by the transponder may then be used to monitor the position of a person or object in a simulated environment.

Tracking systems may be ultrasound, inertial position, or electromagnetic tracking systems, for example. Electromagnetic tracking systems may employ coils as receivers and transmitters. Typically, an electromagnetic tracking system is configured in an industry-standard coil architecture (ISCA). ISCA uses three colocated orthogonal quasi-dipole transmitter coils and three colocated quasi-dipole receiver coils. Other systems may use three large, non-dipole, non-colocated transmitter coils with three colocated quasi-dipole receiver coils. Another tracking system architecture uses an array of six or more transmitter coils spread out in space and one or more quasi-dipole receiver coils. Alternatively, a single quasi-dipole transmitter coil may be used with an array of six or more receivers spread out in space.

The ISCA tracker architecture uses a three-axis dipole coil transmitter and a three-axis dipole coil receiver. Each three-axis transmitter or receiver is built so that the three coils exhibit the same effective area, are oriented orthogonally to one another, and are centered at the same point. If the coils are small enough compared to a distance between the transmitter and receiver, then the coil may exhibit dipole behavior. Magnetic fields generated by the trio of transmitter coils may be detected by the trio of receiver coils. Using three approximately concentrically positioned transmitter coils and three approximately concentrically positioned receiver coils, for example, nine parameter measurements may be obtained. From the nine parameter measurements and one known position or orientation parameter, a position and orientation calculation may determine position and orientation information for each of the transmitter coils with respect to the receiver coil trio with three degrees of freedom.

In medical and surgical imaging, such as intraoperative or perioperative imaging, images are formed of a region of a patient's body. The images are used to aid in an ongoing procedure with a surgical tool or instrument applied to the patient and tracked in relation to a reference coordinate system formed from the images. Image-guided surgery is of a special utility in surgical procedures such as brain surgery and arthroscopic procedures on the knee, wrist, shoulder or spine, as well as certain types of angiography, cardiac procedures, interventional radiology and biopsies in which x-ray images may be taken to display, correct the position of, or otherwise navigate a tool or instrument involved in the procedure.

Several areas of surgery involve very precise planning and control for placement of an elongated probe or other article in tissue or bone that is internal or difficult to view directly. In particular, for brain surgery, stereotactic frames that define an entry point, probe angle and probe depth are used to access a site in the brain, generally in conjunction with previously compiled three-dimensional diagnostic images, such as MRI, PET or CT scan images, which provide accurate tissue images. For placement of pedicle screws in the spine, where visual and fluoroscopic imaging directions may not capture an axial view to center a profile of an insertion path in bone, such systems have also been useful.

Generally, image-guided surgery systems operate with an image display which is positioned in a surgeon's field of view and which displays a few panels such as a selected MRI image and several x-ray or fluoroscopic views taken from different angles. Three-dimensional diagnostic images typically have a spatial resolution that is both rectilinear and accurate to within a very small tolerance, such as to within one millimeter or less. By contrast, fluoroscopic views may be distorted. The fluoroscopic views are shadowgraphic in that they represent the density of all tissue through which the conical x-ray beam has passed. In tool navigation systems, the display visible to the surgeon may show an image of a surgical tool, biopsy instrument, pedicle screw, probe or other device projected onto a fluoroscopic image, so that the surgeon may visualize the orientation of the surgical instrument in relation to the imaged patient anatomy. An appropriate reconstructed CT or MRI image, which may correspond to the tracked coordinates of the probe tip, may also be displayed.

Medical practitioners, for example, rely on electromagnetic trackers to perform sensitive image-guided surgery. Accuracy of position measurement is important when guiding a precision instrument in a patient without a direct line of sight. Distortion may produce inaccurate position measurements and potential danger to a patient. Thus, a system that reduces inaccurate tracking measurements would be highly desirable. A system that minimizes the effect of distortion on position measurement would be highly desirable.

Distortion may be introduced into an image from magnetic fields generated by tools, sensors, and the examination or operating environment, for example. Current systems typically correct for distortion by mapping position and orientation of the distorting object. Position mapping uses a model that ignores the distortion and corrects for the distortion of the position and orientation of the distorting object are modeled. However, a model and correction scheme that ignore the effects of distortion in the model are inefficient and inaccurate. Thus, a system and method for improved distortion modeling and correction would be highly desirable.

Additionally, when mapping position and orientation of a distorter, a differential method is used. That is, the magnetic field is measured on the surface of the distorter. Then, a series of differential calculations are computed to determine a table of values representing the interior of the volume. That is, a field is measured at the surface of the volume and differential equations are directly solved for the interior of the volume to construct a look-up table model. Such a look-up table determination involves a large number of calculations. Thus, a simplified method for determining field distortion of a volume would be highly desirable.

Thus, there is a need for an image-guided navigation system and method for improved distortion mapping using integral methods.

BRIEF SUMMARY OF THE INVENTION

Certain embodiments of the present invention provide a system and method for improved distortion measurement and compensation. Certain embodiments of a method include selecting a set of sources on a surface of a volume, determining mutual inductances from the set of sources on the surface, and calculating distortion from the volume using the mutual inductances from the set of sources on the surface.

In an embodiment, distortion is calculated using an integral method and/or a finite element analysis. The volume may be modeled as a simplified construct, such as a ring model, a coil array with straight line segments model, a polygon model, and/or dipole array model. The model may be adjusted based on the distortion calculated from the volume.

Certain embodiments of a method for electromagnetic tracking with distortion compensation include identifying a distorter volume in a tracking coordinate system, selecting a model to represent the distorter volume in the tracking coordinate system, measuring a subset of a surface of the distorter volume, and mapping a magnetic field generated by the distorter using the model and measurements of the subset of the surface. In an embodiment, model parameters are adjusted based on the measurements. The model may include a ring model, a coil array with straight line segments model, a polygon model, and/or a dipole array model. The mapping may include using an integral method and/or a finite element analysis, for example. In an embodiment, the magnetic field is mapped based on an approximate set of field sources on a surface of the distorter and adjusted using at least one of an integral method and a finite element analysis. In an embodiment, measurements may be obtained using a plurality of positions on the surface and one orientation. In an embodiment, the tracking coordinate system may be characterized using a robot. Additionally, an object may be tracked using the mapping of the magnetic field.

Certain embodiments of an electromagnetic tracking system include a distortion measurement module measuring data from a plurality of mutual inductance sources located on a surface of a volume, a calculation module calculating distortion from the volume using the plurality of mutual inductance sources at least one of an integral method and a finite element analysis, and a mapping module mapping a magnetic field around an object, the mapping including effects of the distortion. In an embodiment, the integral method includes use of a Green's function to calculate distortion. The system may also include a tracking module for tracking the object using the magnetic field mapping.

In an embodiment, the distortion measurement module approximates the volume using a model. The model may include a ring model, a coil array with straight line segments model, a polygon model, and/or a dipole array model. The parameters of the model may be adjusted based on measurements from the volume. In an embodiment, the distortion measurement module obtains measurements using a plurality of positions on the surface and one orientation. The distortion measurement module may also measure magnetic fields from the plurality of sources located on the surface of the volume.

Figure 1:
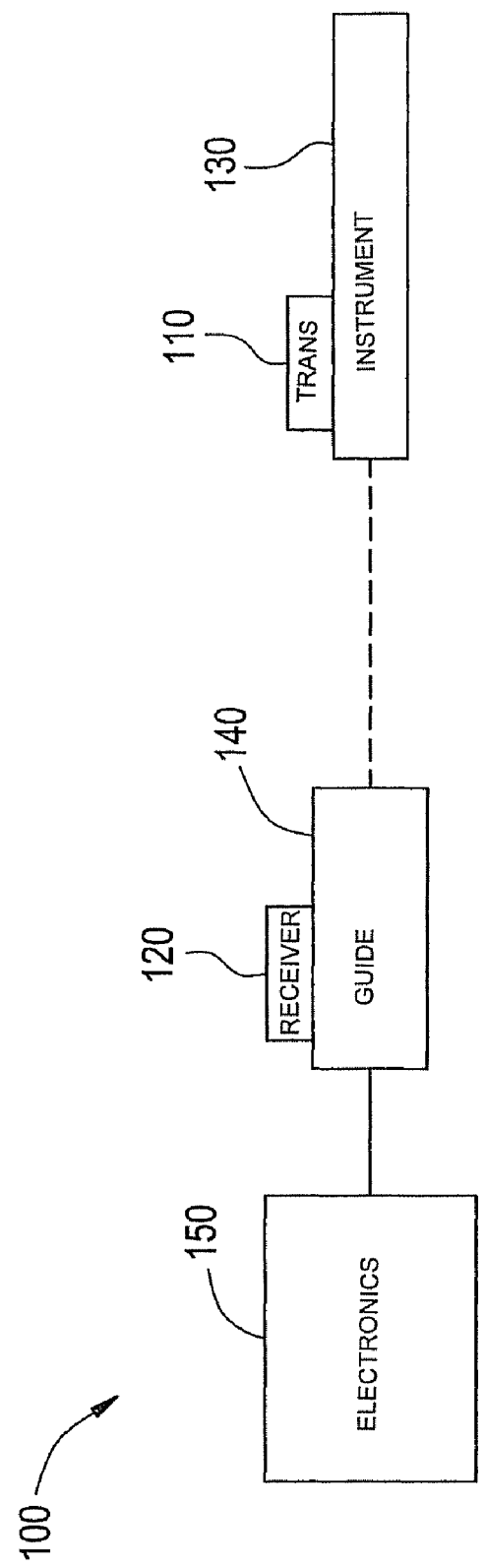
FIG. 1 illustrates an electromagnetic tracking system used in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

For the purpose of illustration only, the following detailed description references a certain embodiment of an electromagnetic tracking system used with an image-guided surgery system. It is understood that the present invention may be used with other imaging systems and other applications.

FIG. 1 illustrates an electromagnetic tracking system 100 used in accordance with an embodiment of the present invention. The tracking system 100 includes a transmitter 110, a receiver assembly 120, an instrument 130, an instrument guide 140, and a tracker electronics 150. The transmitter 110 may be a wired or wireless transmitter. In an embodiment, the wireless transmitter 110 is positioned on the instrument 130. The receiver assembly 120 is located remotely from the instrument 130 and the transmitter 110. The instrument guide 140 is used to control the instrument 130.

In an embodiment, the tracker electronics 150 includes a Lucas 4650 processor. The tracker electronics 150 may be integrated with the receiver assembly 120 or may be a separate module, for example. In an embodiment, the tracker electronics 150 resides on a receiver assembly 120 board to perform calculations on signal data.

In an embodiment, the receiver assembly 120 includes two receivers 122, 124. The receivers 122, 124 of the receiver assembly 120 may be receiver dipole coils or coil trios, for example. The receiver assembly 120 may be attached to the instrument guide 140. The instrument 130 may be a surgical drill or other medical instrument, for example. The instrument guide 140 may be a drill guide or other medical instrument guide, for example. In another embodiment, the instrument 130 with instrument guide 140 may be a tool that is indirectly controlled for applications wherein an operator's field of vision is obscured by an object.

In certain embodiments, the transmitter 110 is attached to the instrument 130. Alternatively, the transmitter 110 may be integrated with the instrument 130. Using the transmitter 110 and receiver assembly 120, the position of the instrument 130 is tracked with respect to the instrument guide 140 or other reference point, for example.

The system 100 may also include one or more additional transmitters (not shown) for use in instrument 130 tracking. The additional transmitter(s) may be wired or wireless transmitter(s). For example, a wireless second transmitter may be located on the instrument guide 140 or on the instrument 130. Alternatively, for example, a wired second transmitter may be located on the instrument guide 140. The second transmitter may be wired to the tracker electronics 150. A cable may be run from the instrument 130 to the tracker electronics 150. The transmitter 110 and additional transmitter(s) may be tracked simultaneously from the receivers in the receiver assembly 120.

In an embodiment, the transmitter 110 is an ISCA transmitter, such as a wireless ISCA transmitter coil trio, for example. The transmitter 110 eliminates the need for a cable connecting the instrument 130 to the tracker electronics 150. Software running with the tracker electronics 150 may be reconfigured to accommodate a wired or wireless transmitter. The transmitter 110 may draw power from the instrument 130 or may have a separate power source, for example. The transmitter 110 may be tracked from each of the receivers in the receiver assembly 120. Thus, certain embodiments use a transmitter 110 and a wired receiver assembly 120 to track the position of the instrument 130 with respect to the instrument guide 140.

In an embodiment, a gain ratio of the signal received from the transmitter 110 is known but an absolute gain in the receiver assembly 120 may not be known. The tracker electronics 150 may determine the transmitter 110 position with respect to the instrument guide 140 or other reference point. The direction or orientation of the transmitter 110 position may be determined from the received signals and gain ratio. However, a tracked position of the transmitter 110 may have range errors (i.e., the tracked position is in the right direction but not at the right distance). To determine a correct range, the tracker electronics 150 may triangulate on the tracked positions of the transmitter 110 from the receivers and use the positional relationship between the two receivers 122, 124 in the receiver array 120.

As an example, the instrument 130 may be a surgical drill. The instrument guide 140 is a drill guide for the drill. The transmitter 110 includes a coil trio and transmission electronics is located on the drill. The receiver assembly 120 is located on the drill guide. The receiver assembly 120 includes two receiver 122, 124 coil trios. The instrument 130, transmitter 110, receiver assembly 120, and other components in the environment may act as distorters and interfere with tracking accuracy.

Figure 2:
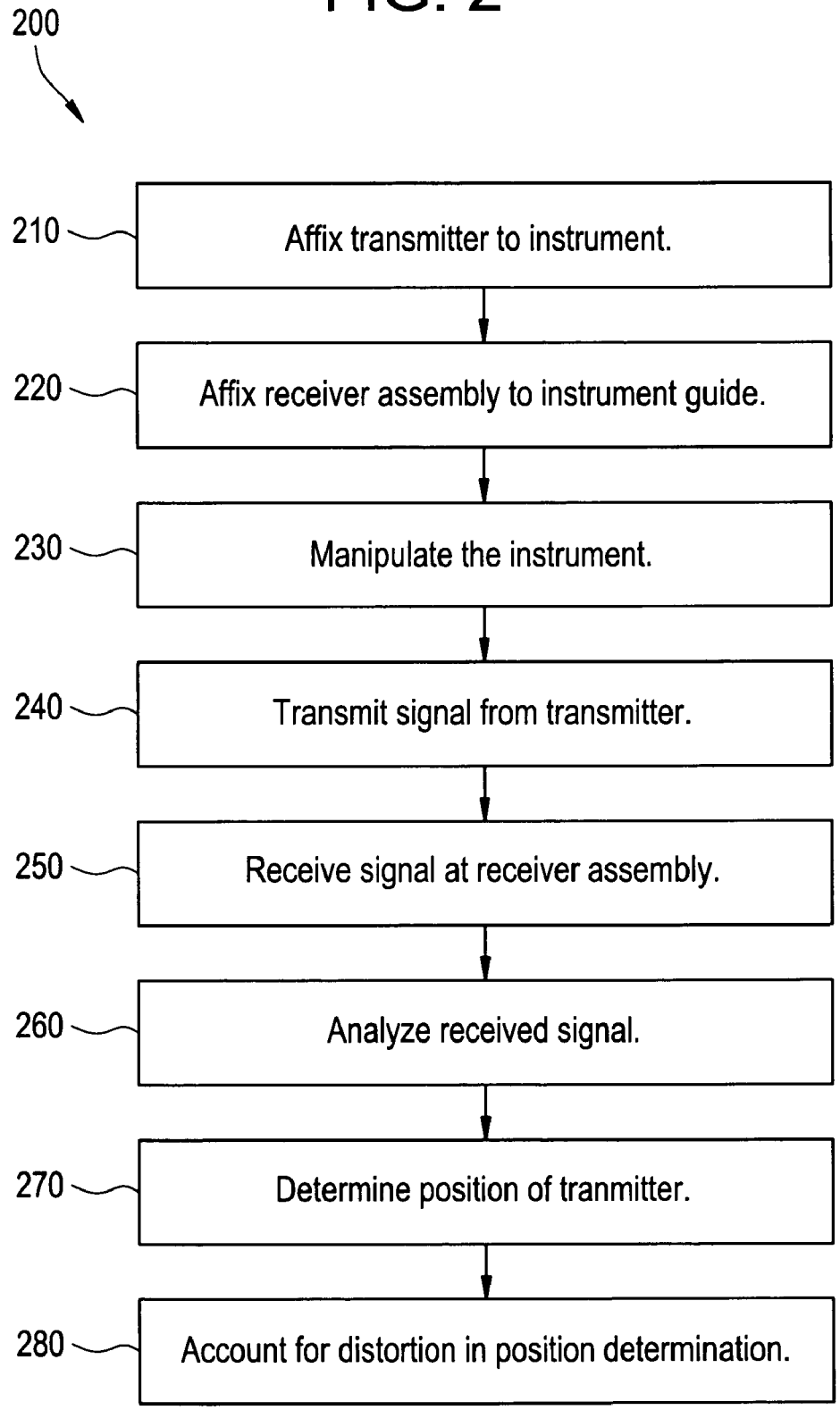
FIG. 2 illustrates a flow diagram for a method for tracking a position of an instrument used in accordance with an embodiment of the present invention.

FIG. 2 illustrates a flow diagram for a method 200 for tracking a position of an instrument 130 used in accordance with an embodiment of the present invention. First, at step 210, the transmitter 110 is affixed to an instrument 130, such as a surgical drill or other medical instrument or tool. Next, at step 220, the receiver assembly 120 is affixed to the instrument guide 140. In an embodiment, the transmitter 110 includes a transmitter coil trio. In an embodiment, the receiver assembly 120 includes two receiver 122, 124 coil trios.

Then, at step 230, an operator manipulates the instrument 130 inside the patient using the instrument guide 140. At step 240, the transmitter 110 broadcasts a signal using power from the instrument 140. For example, the electronics of the transmitter 110 generate a signal using the coil of the transmitter 110.

Next, at step 250, the receivers of the receiver assembly 120 detect the signal transmitted from the transmitter 110. At step 260, the received signals are analyzed. The tracker electronics 150 measure the signals as received by the receivers 122, 124. The signals are measured based on the relationship between the receivers 122, 124 in the receiver assembly 120.

Figure 3:
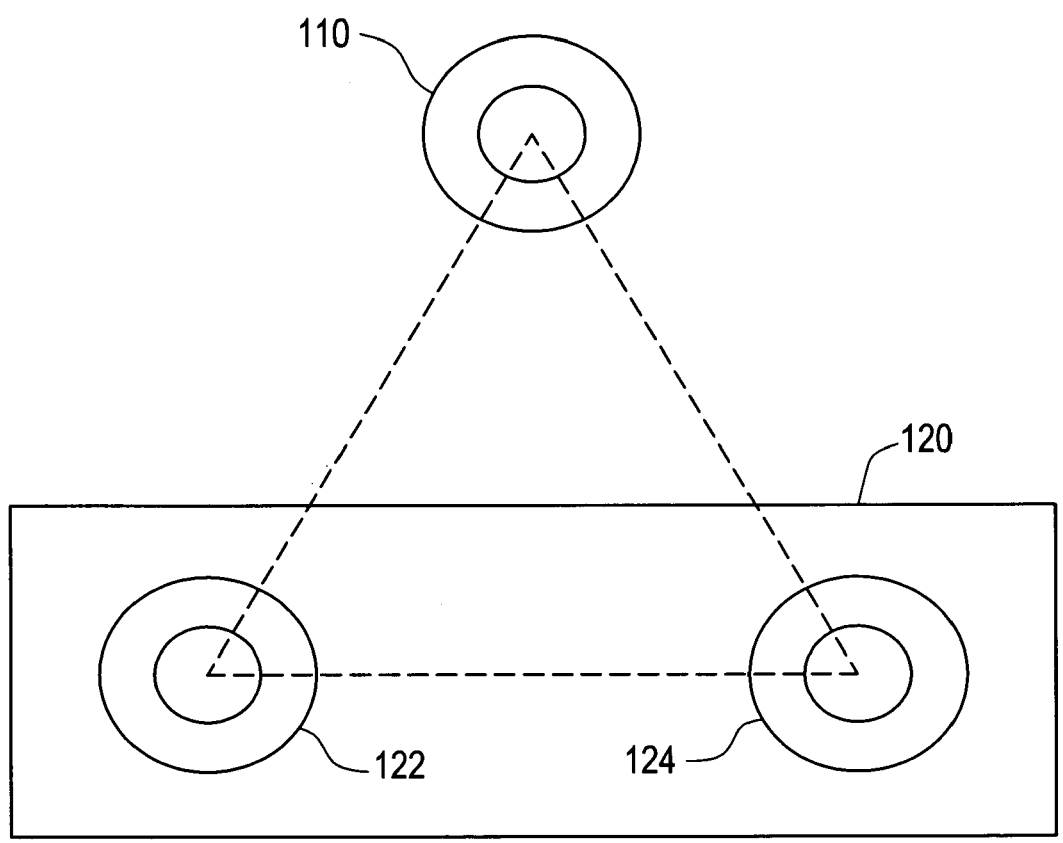
FIG. 3 illustrates triangulation between a wireless transmitter and two receivers in a receiver assembly used in accordance with an embodiment of the present invention.

Then, at step 270, the position of the transmitter 110 is determined. The transmitter 110 position may be determined with respect to the instrument guide 140 or other reference coordinate system. The direction or orientation of the transmitter 110 position may be determined from the received signals. As illustrated in FIG. 3, triangulation may determine a range to the transmitter 110 based on the tracked positions of the transmitter 110 from the receivers and on the positional relationship between the two receivers 122, 124 in the receiver array 120. In an alternative embodiment, multiple transmitters transmit signals to the receiver assembly 120 to help locate the instrument 130. At step 280, distortion may be accounted for in the position determination. For example, integral (e.g., Green's function) or differential (e.g., finite-element) methods may be used to determine an impact of field effects from a distorter on the tracked position of the transmitter 110.

In one embodiment, one or more precision transmitter 110 drivers are used to drive an ISCA transmitter 110 so that the system exhibits three orthogonal dipole magnetic moments of equal magnitudes and nominal signs. Thus, characteristics of the dipole coils, such as the transmitter 110 coil and receiver 122, 124 coils, may be determined except for a global gain. Therefore, position and orientation (P&O) solutions may include a range error but otherwise be accurate. That is, in an embodiment, performing an ISCA P&O calculation for each receiver coil trio produces P&O results that are accurate except for a common range scale factor error. Adding a precision reference allows control of global gain. However, the gain of the receiver assembly 120 and/or tracker electronics 150 may not be precisely known.

In an embodiment, two receiver 122, 124 coil trios in the receiver assembly 120 and the transmitter 110 form a triangle. Angles of the triangle may be determined. Thus, ratios of the sides of the triangle may also be determined. Additionally, spacing between the two receivers 122, 124 may be determined. The spacing between the receivers 122, 124 represents one side of the triangle. A range scale factor that corresponds to the spacing between receivers 122, 124 may be calculated. The range scale factor may be used to correct the P&O calculation. The range scale factor may be used to correct the measurement of the length between the receivers 122, 124 to generate an accurate P&O for the transmitter 110.

In another embodiment, one or more non-precision transmitter 110 drivers are used to drive a transmitter coil trio to produce three transmitter dipole moments that are approximately orthogonal and of approximately equal magnitudes. That is, the transmitter coils are preferably designed with approximately nominal gains and are approximately orthogonal. The non-precision drivers drive the transmitter coil trio with nominal waveforms to give the desired fundamentals and second harmonics for an approximately nominal transmitter coil trio.

A nominal transmitter coil is perfectly orthogonal with nominal coil gains and nominal signs for the coil trio. The nominal gains of the nominal coil trio are different, since the coils are of slightly different nominal sizes (for example, the coils nest in one another). In an embodiment, the transmitter 110 and other transmitters in the system 100 are built with approximately nominal gain and approximately perfect orthogonality. However, signs of the coil gains for the transmitter coil trio may not be controlled.

In an embodiment, the signs of the coil gains may impact the P&O determination. If two signs are reversed, the coil trio will appear to be rotated 180 degrees. A rotation by 180 degrees changes an even number of signs. A mirror-image (known as a perversion in optics) operation may change one or all three signs.

A solution fitter may be applied to determine a goodness of fit of coil gain and sign. Then, the sign on one gain may be reversed. The solution fitter is rerun with the sign of one gain reversed to obtain a second goodness of fit measurement. The solution providing a better goodness of fit is selected. For some solution fitters or solvers, the fitter may not find a solution for one of the two gain cases, corresponding to an impermissible rotation. If one solution is not found, the other solution is used.

Distortion effects may also factor into a goodness of fit determination. Rather than employing a traditional differential method to perform numerous calculations to generate a look-up table of field values for an interior of a volume based on field measurements at the surface of the volume, integral methods may be used to map magnetic fields or mutual inductances generated by a volume. In an embodiment, an integral method involves fewer calculations than a differential method. An integral method may be used to directly map fields or mutual inductances of a volume rather than map position and orientation of the volume to later determine fields causing distortion. With position mapping, a model is used that ignores the distortion and later corrects for that distortion. With field or inductance mapping, mapping is done with a model that includes effects of distortion. Therefore, measurements using the field/inductance mapping model offer improved accuracy. Additionally, distorters may be modeled as objects of equivalent shape to simplify calculations and improve determination speed.

A variety of objects may be used as mathematical models of distorters. For example, a ring, one or more arrays of coils with straight-line segments in them, or one or more arrays of dipoles may be mathematical magnetic field models. By modeling a distorter, such as a shield can, an instrument, or a table, as a simpler, known construct, assumptions may be made when analyzing magnetic fields radiated by the distorter. A metal shield can around an image intensifier may be modeled as a metal ring, for example.

In an embodiment, a ring model is used for integral field mapping for a distorting volume. A mathematical model may be constructed in the approximate shape of the distorter and then adjusted. Parameters of the model are measured and then adjusted to determine a best fit. For example, parameters may include a position in space, a center of the ring, a tilt of the ring, a size of the ring, and/or a diameter of the wire that makes the ring.

In an embodiment, a relatively small number of parameters are measured and adjusted. The parameters for the ring model are relatively easy to adjust. In an embodiment, parameters of the model and the tracking system may be adjusted using a mapping chamber. In another embodiment, parameters of the model and mapping system may be adjusted on-site. For example, a simple robot or fixed array of coils of known or predetermined configuration may be used to adjust system and model parameters on-site to improve field mapping accuracy. An example of a robot is a non-conductive and non-ferromagnetic robot, such as a plastic or glass robot. The robot may be a two-dimensional robot providing a plane for measurement. Alternatively, a three-dimensional robot provides a volume for measurement.

An operator or technician may use a portable robot or coil array at a hospital, for example, to calibrate a field mapping or distortion handling system. The robot or coil array may be placing on an examination or operating table. Then, measurements may be obtained using the robot or coil array. For example, a shape of transmit and receive coils in a coil array or robot is known. The robot is moved around to characterize the volume. In an embodiment, the robot is a plane robot. In an embodiment, rather than measuring an entire surface, a selected plane may be measured. Distortion for the surface may be determined using the measurements. The system may then be calibrated based on the distortion measurements produced by the robot or coil array of known configuration.

In an embodiment, a receiver moves within a field-measurement volume, with a transmitter and distorter located outside of the volume. Therefore, no field sources are present in the interior of the volume of interest. Components of magnetic fields or mutual inductances that are perpendicular to the volume boundary of surface are measured all over the surface of the volume. From the field or inductance measurements, the field or mutual inductance for a volume may be calculated at all points in the interior of the volume using various methods.

For example, a finite-element or differential method may be used to calculate interior volume fields/inductances. Using the perpendicular or normal component of the field/inductance at the surface of the volume and a mesh of points defined in the interior of the volume, a Laplace equation may be numerically solved in the interior to determine vector potential. Interior magnetic field/inductance may then be calculated from the vector potential.

As another example, a boundary element or integral method may be used to calculate interior magnetic field or mutual inductance for a volume. First, Green's functions (spatial impulse responses), for example, are calculated for an interior shape of the volume boundary. Then, the normal component of the field or mutual inductance is measured at a plurality of points over the volume boundary. Interior field or mutual inductance for the volume is then calculated by integrating the normal component measurements and the Green's functions.

In an embodiment, magnetic field and/or mutual inductance mapping may be determined using integral methods. For example, the field or mutual inductance may be mapped using a three-dimensional array of functions, such as Green's functions. A distorter is identified, and the effects of the distorter are measured. Then, a model is determined for the distorter and its effects. For example, an operating table includes metal. Thus, the table may be built so that the composition and distortion effects are "known," or the table may be built and then measured to determine distortion effects.

Green's functions or similar functions are useful in solving boundary value problems. Green's functions may be used in an integral or integral transform to solve an equation with boundary conditions. A Green's function provides the field at a given point due to a field source at the point. Then the field in the interior of a volume for any set of field measurements on the boundary is a sum of the Green's functions, each multiplied by the actual field measurement at the boundary point corresponding to the respective Green's function. Thus, Green's functions may be used in calibration to determine the amount of distortion at the surface of the volume rather than determining field effects inside the volume which do not affect the surrounding environment.

Green's functions separate field/inductance calculations into two parts. A first calculation or set of calculations is based on a shape of a surface being measured over. After the first calculation is completed, a second calculation or set of calculations are computed using the same shape on a different distorter. For example, a ring or coil array with straight line segments may be used as a model shape. The selected model may be adjusted to better fit the particular distorter based on measurements from the distorter. If sources of magnetic fields and/or mutual inductances are determined, a magnetic field or mutual inductance may be determined at any point. In an embodiment, an approximate set of sources is selected and then adjusted based on obtained measurements (i.e., an integral method). In an alternative embodiment, a mapping chamber is used to map and model magnetic fields/mutual inductances and distorters.

Thus, in an embodiment, field or inductance calculations may be performed repeatedly with a fixed field-measurement volume and transmitter while varying a distorter. For the finite-element method, the whole calculation is repeated for each new distorter. Using the integral method with Green's functions, the calculation is split into two steps. The first step involves a calculation depending upon a shape of a boundary of the volume and not on the distorter or the transmitter (e.g., calculating the Green's functions). The second step involves a shorter calculation depending on the result of the first calculation and on characteristics of the distorter and transmitter. Therefore, the first calculation may be done once for a given boundary, and the second calculation may be repeated for each distorter.

Figure 4:
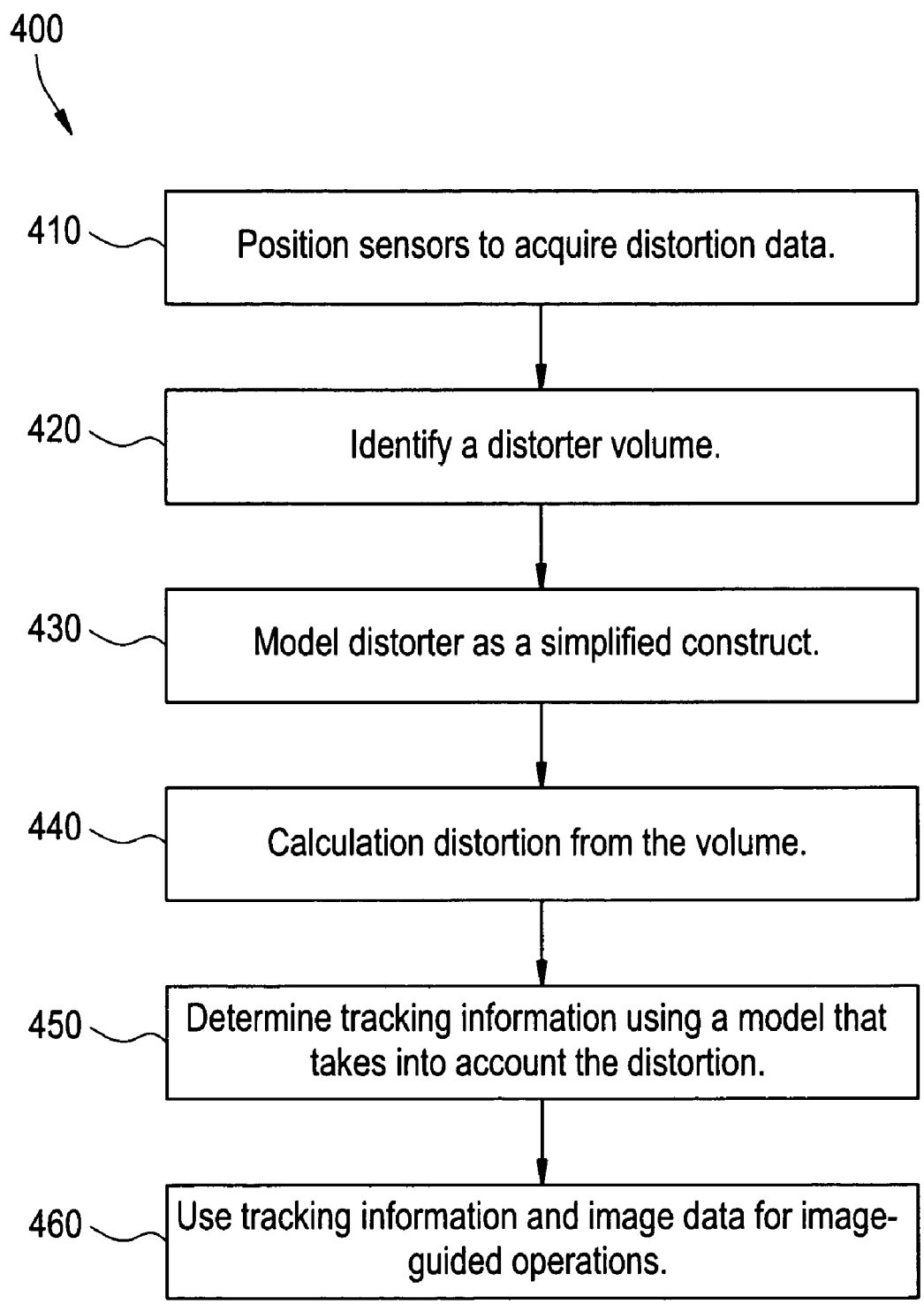
FIG. 4 illustrates an improved method for electromagnetic tracking in accordance with an embodiment of the present invention.

FIG. 4 illustrates an improved method 400 for electromagnetic tracking in accordance with an embodiment of the present invention. First, at step 410, sensors are positioned to acquire distortion data. Next, at step 420, a distorter volume is identified. Then, at step 430, the distorter volume is modeled as a simplified construct, such as a ring or line model. At step 440, distortion from the volume is calculated using the set of sources on a surface of the model in an integral method. As described above, integrals including Green's functions, for example, may be used to identify point sources of distortion in the volume and calculate the distortion generated by the volume to affect the imaging system and/or tracking system.

Then, at step 450, tracking information is determined using a model that accounts for distortion measured from the volume. Tracking information may include a position and orientation of an object being tracked. A model of distorters affecting measurement of tracking information allows distorters to be accounted during measurement, rather than ignoring effects for distortion and later correcting for such effects. That is, tracking information may be obtained by initially accounting for magnetic field or mutual inductance distortions, rather than adjusting tracking data to account for distortion after the tracking data has been acquired. Next, at step 460, tracking information may be used in conjunction with image data for image-guided operations. For example, tracking data from a sensor mounted in a drill may be used in conjunction with a set of patient images to perform image-guided surgery on the patient using the drill.

For example, for a volume, the normal component of a magnetic field is measured over all or a closest part of a boundary of the volume. Then, one or more physically-appropriate source models are selected for the volume. Next, the source model is adjusted to mach the measurements from the volume boundary. The model may then be used for robot characterization of a system. Alternatively, mutual inductance effects may be measured rather than magnetic fields.

Magnetic fields are generated by currents flowing through circuits. Changing magnetic fields are measured by voltages induced in the circuits. A circuit may be defined as a closed electrically-conductive path. A coil is an example of a circuit. An electrically-conductive object, for example, is an example of a set of circuits. A ferromagnetic object may be modeled using circuits on the surface of the ferromagnetic object, for example. Tracker electronics may measure mutual inductances between coils. Thus, in an embodiment, objects may be modeled as arrays of circuits existing in air-filled space. Mutual inductance between two closed circuits may be defined by Neumann's or Maxwell's formula, for example. For example, a mutual inductance Lm between a circuit t and a circuit r may be calculated as follows:

$$L_m = \frac{U_O}{4\pi} \int \int_r \frac{\overline{dsr} \cdot \overline{dst}}{Rtr}, \tag{1}$$

where $U_O$ is a permeability of free space, $\overline{dst}$ is a length element vector of circuit t, and $\overline{dsr}$ is a length element vector of circuit r, and "." is a dot product of two vectors. The mutual inductance of the two coils (e.g., transmitter and receiver) is a geometrical property of the two circuits or coils, t and r, and positions and orientations of the circuits or coils in space.

Mutual inductance is also an electrical property that may be measured using alternating current:

$$V = Lm\frac{dI}{dt}, \tag{2}$$

where I is a current applied to one coil, and V is a voltage induced in another coil. If both circuits are composed of straight-line segments, one of the integrals in Equation (1)

may be calculated numerically. If both circuits are small, both circuits may behave like dipoles, resulting in the following:

$$Lm = \frac{K}{S^3}(3(\bar{t}.\bar{s})(\bar{r}.\bar{s}) - (\bar{t}.\bar{r})), \quad (3)$$

Lm is a mutual inductance between dipole t and dipole r, $U_O$ is a permeability of free space, "." is a dot product of two vectors, $$K = \frac{U_O AefftAeffr}{4\pi},$$

$\bar{S}$ is a vector from dipole circuit t to dipole r, S is a magnitude of $\bar{S}$, $\bar{s}$ is a unit vector in the direction of $\bar{S}$, $\bar{S}=S\bar{s}$, $\bar{t}$ is a unit vector in a direction of $\overline{Aefft}$, Aefft is a magnitude of an effective area of dipole t, $\overline{Aefft}$ is an effective area of dipole t, $\bar{r}$ is a unit vector in a direction of $\overline{Aeffr}$, Aeffr is a magnitude of an effective area of dipole r, and $\overline{Aeffr}$ is an effective area of dipole r.

If one circuit is small, that circuit behaves like a dipole and Equation (1) reduces to an expression of a transmitter magnetic field divided by current dotted with a dipole receiver:

$$Lm=(\overline{Bt}/I).\overline{Aeffr} \quad (4),$$

where Lm is a mutual inductance between a circuit t and a dipole circuit r, I is a current flowing in circuit t, $\overline{Bt}$ is a vector magnetic field due to current I flowing in circuit t at a location of dipole r, "." is a dot product of two vectors, $\bar{r}$ is a unit vector in a direction of $\overline{Aeffr}$, Aeffr is a magnitude of an effective area of dipole r, and $\overline{Aeffr}$ is a vector effective area of dipole r. Note that Equation (1) does not distinguish between transmitter and receiver, so the dipole in Equation (4) may be the receiver or the transmitter. When the dipole in Equation (4) is the receiver, the field expression is the magnetic field due to a unit current flowing in the transmitter circuit. When the dipole in Equation (4) is the transmitter, the field expression is not the magnetic field but does obey the magnetic field equations (the law of reciprocity).

The magnetic field of a unit current in a circuit that may not be modeled as a dipole may be expressed in a variety of ways. For a circular circuit, the field may be expressed in a ring model using elliptical intervals, as described in U.S. Patent Application Publication No. 20030184285, filed on Mar. 27, 2002, entitled "Magnetic tracking system," which is herein incorporated by reference. For a circuit composed of finite-length straight-line segments, a closed-form expression may be derived. Alternatively, a circular ring may be approximated with a many-sided polygon, and each side of the polygon may be modeled using finite-length straight-line segment expressions.

If both coils are almost, but not quite, small enough for dipole models the following approximation may be used to speed up inductance calculation for a pair of coils, t and r. A dipole model may be used to calculate partial derivatives, and a double integral model may be used for nominal mutual inductances. For example, a mutual inductance ("Lm_td_rd") may be calculated using a dipole model (Equation (3)) for both coils. Then, a mutual inductance ("Lm_ts_rd") may calculated with t as a current segment and r as a dipole (Equation (4)). Another mutual inductance ("Lm_td_rs") may be calculated using dipole t and current segment r. Then, a mutual inductance ("Lm_ts_rs") may be calculated using a current segment model for both coils (Equation (1)). The mutual inductance Lm_ts_rs may be approximated as:

$$Lm\_ts\_rs=Lm\_ts\_rd+Lm\_td\_rs+Lm\_td\_rd \quad (5).$$

The approximation may be useful in a variety of situations or environments. For example, if the coils have corners and are of similar sizes, Equation (5) provides a fast and accurate solution. Equation (5) provides a fast and accurate solution even when coils surround ferrite or other metal cubes or when transmitter and receiver coils are positioned in close proximity to one another.

If one circuit is not tiny, but is a single turn coil, mutual inductance for the circuit may be calculated by integrating over an area enclosed by the turn:

$$Lm=\int((\overline{Bt}/I).d\overline{A}) \quad (6),$$

where Lm is a mutual inductance between circuit t and single-turn circuit r, I is current flowing in circuit t, $\overline{Bt}$ is a vector magnetic field due to current I flowing in circuit t at location of dipole r, "." is the dot product of two vectors, $d\overline{A}$ is a differential of vector effective area, and the integral is over a surface bounded by the single-turn circuit r.

For a coil modeled as a sum of individual single-turn sub-coils (such as a coil with corners modeled as five rectangular planar coaxial single-turn coils), mutual inductance may be expressed as follows:

$$Lm = \sum_N \int_N ((\overline{Bt}/I) \cdot d\overline{A}), \quad (7)$$

where Lm is a mutual inductance between circuit t and multi-turn circuit r, N is an index for the sum and numbers the subcoils, I is current flowing in circuit t, $\overline{Bt}$ is a vector magnetic field due to current I flowing in circuit t, "." is the dot product of two vectors, $d\overline{A}$ is a differential of vector effective area for subcoil(N), and the integral is over a surface bounded by each single-turn subcoil(N). In Equation (7), subcoils may not be planar, rectangular, of a same shape, parallel, and/or coaxial. Equation (7) provides a flexible formula for mutual inductance calculation.

In an embodiment, a size and shape of a coil are approximately determined. A gain of a cable between the coil and electronics may also be approximately determined. Thus, the coil is characterized to measure the coil gain (nominally unity, for example) assuming nominal shape and size. Thereafter, modeled mutual inductances may be scaled by the coil gain.

For example, a system may include a transmitter coil, a receiver coil, and a conductive ring. The conductive ring distorts a magnetic field due to eddy currents induced in the conductive ring. The ring may be a single-turn ring or as a more complex ring, for example. The conductive ring may be modeled as a distorter coil, for example. Then, a plurality of mutual inductances may be determined. For example, a mutual inductance between the transmitter and receiver may be calculated with the distorter present ("Lm_total"). A mutual inductance between the transmitter and receiver may be calculated without the distorter present ("Lm_tr"). Mutual inductances may also be calculated between the transmitter and the distorter ("Lm_td") and between the distorter and the receiver ("Lm_dr"). A self-inductance of the distorter ("Ls_d") may be calculated as well. Mutual inductances Lm_tr, Lm_td, and Lm_dr may be calculated as described above. Then, Lm_total may be calculated as $$Lm\_total=Lm\_tr+(Lm\_td*Lm\_dr/Ls\_d) \quad (8).$$

If the distorter is a perfect conductor, the self-inductance of the distorter Ls_d is real. If the distorter is an imperfect conductor, then the self-inductance of the distorter may be considered to be complex and frequency-dependent, where an imaginary part of the self-inductance accounts for losses in the distorter. Phase shift may lead to a complex Lm_total. The self-inductance of the distorter may be determined approximately by calculation. However, a precise value for Ls_d may be determined by mutual inductance distortion mapping. If a distorter ring is circular, for example, the ring may be modeled as a regular polygon.

In an embodiment, distortion, such as distortion caused by a metal flouro can surrounding an image intensifier, may be mapped using a robot arm in a measurement volume. A transmitter coil is mounted on the robot arm, and a receiver coil is attached to the distorter can. The transmitter and receiver coils are characterized for size, shape and gain, for example, including effects of connecting cables.

Traditional distortion mapping ignores mutual inductances and instead corrects a position and orientation output by a tracker. This position and orientation detection involves collecting undistorted tracker position and orientation outputs at every point in the measurement volume with the distorter removed, and then collecting distorted tracker output again at every point in the measurement volume with the distorter present. Then, a numerical mapping is constructed from undistorted points to corresponding distorted points.

Distortion mapping mutual inductances or magnetic fields reduces the number of data points to be collected. Magnetic fields may be related to mutual inductances using equations, such as Equations (4), (6) and (7). For a finite-element method (differential method) and integral method (Green's function method) of field or mutual inductance mapping, data is collected at all points on a boundary of the measurement volume. In an embodiment, for mutual inductance modeling, collecting data on points on the X=0 face of the measurement volume (the face that places the transmitter closest to the receiver and distorter) is sufficient for distortion mapping. The mutual inductance model may allow assumptions about the distorter resulting in a few parameters to be fitted.

In an embodiment, to perform mutual inductance mapping, the transmitter and receiver coils are precisely characterized for size, shape, and gain, including effects of connecting cables. Then, mutual inductance data is measured at every robot arm position on the X=0 plane. Next, initial estimates are determined for transmitter orientation and receiver position in relation to the robot arm. Initial estimates are determined for distorter ring model ring position, ring orientation, ring diameter, and ring self-inductance, for example. For each data point, estimated mutual inductance, Lm_total, is calculated using Equation (8), for example. Then, the initial estimates are adjusted, and the Lm_total calculations repeated to minimize differences between estimated and measured mutual inductances. In an embodiment, mutual inductances are multiplied by range before minimizing the differences to account for the distance between the transmitter and receiver. The plurality of mutual inductance measurements are used to form a distortion map for the measurement volume.

Figure 5:
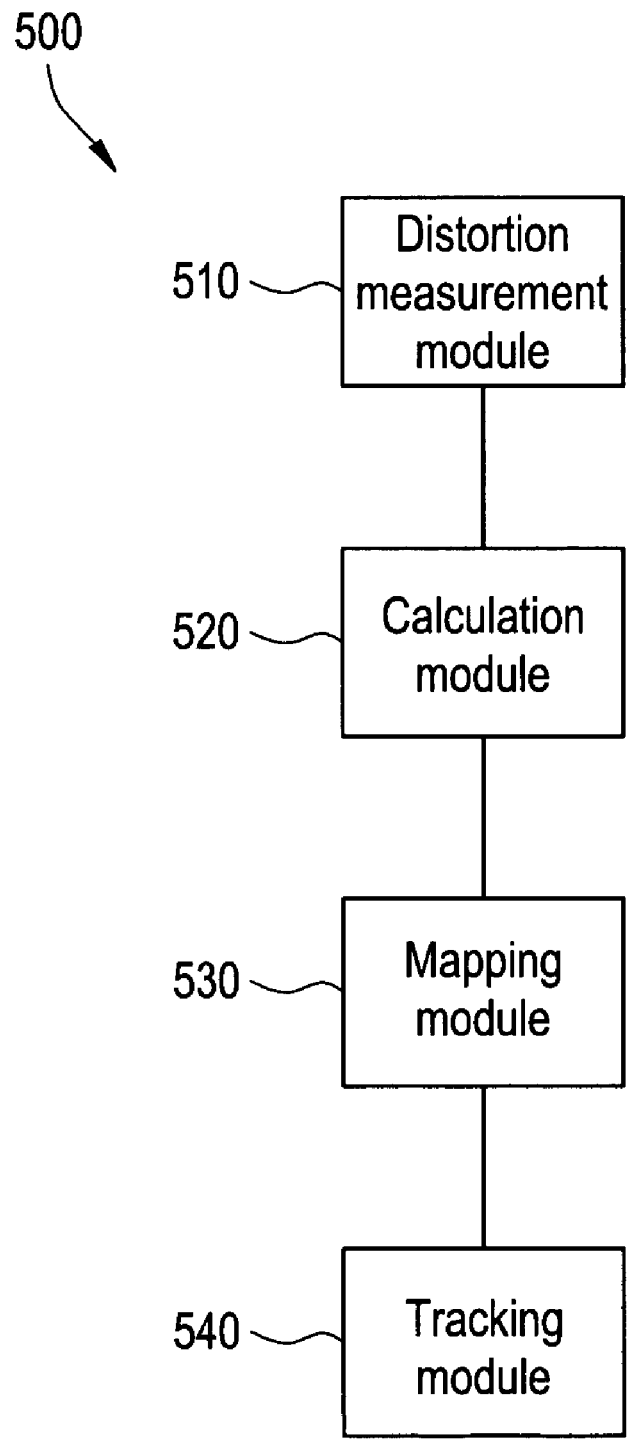
FIG. 5 illustrates an improved electromagnetic tracking system used in accordance with an embodiment of the present invention.

FIG. 5 illustrates an improved electromagnetic tracking system 500 used in accordance with an embodiment of the present invention. The system 500 includes a distortion measurement module 510, calculation module 520, a mapping module 530, and a tracking module 540. The distortion measurement module 510 measures data from a plurality of magnetic field sources located on a surface of a volume. The calculation module 520 calculates distortion from the volume using the plurality of magnetic field sources in an integral method. The mapping module 530 maps a magnetic field around an object. The mapping from the mapping module 530 includes effects of the distortion. The integral method may include the use of a Green's function to calculate distortion.

In an embodiment, the distortion measurement module 510 approximates the volume using a model. The model may be a ring model, a coil array with straight line segments model, and a dipole array model, for example. In an embodiment, a ring model may be modeled as a polygon including a plurality of straight segments.

Parameters of the model may be adjusted based on measurements from the volume to better describe the volume and/or a set of field sources on the surface of the volume. The tracking module 540 tracks the object using the magnetic field mapping. The improved electromagnetic tracking system 500 may be used to track an object for image-guided operations, for example, using a simplified integral method and distorter modeling.

Thus, certain embodiments allow quicker, more simplified determination of tracking position and orientation while accounting for distortions using integral methods or finite element analysis. Measurements may be obtained from a plurality of positions on a volume boundary using a single orientation. Certain embodiments utilize simplified distortion models to determine distortion effects caused by a volume, rather than attempting to analyze the entire contents of the volume. Modeling a distorter allows measurement of a small part of a volume surface. Measurements may be matched with the model. Then a smaller number of parameters may be adjusted to accurately model the distorter, rather than redoing an entire surface measurement with each change in distorter. Certain embodiments provide for distortion mapping by collecting mapping data at one orientation at each of various positions on a surface of a measurement volume rather than collecting mapping data at various orientations at each of various positions throughout the measurement volume. Certain embodiments utilize mutual inductance measurements, rather than magnetic field measurements, for improved distortion determination. Mutual inductance measurement, unlike magnetic field measurement, may occur independent which coil is inducing the fields. Mutual inductance measurements may then be correlated with magnetic field measurements.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for electromagnetic tracking, said method comprising:
   selecting a set of sources on a surface of a volume;
   determining mutual inductances from said set of sources on said surface with a distortion measurement module;
   calculating distortion from said volume using said mutual inductances from said set of sources on said surface with a calculation module, wherein said distortion is calculated using an integral method and a finite element analysis; and
   tracking an object with a tracking module, wherein said tracking comprises accounting for said distortion during measurement of tracking information.

2. The method of claim 1, further comprising modeling said volume as a simplified construct.

3. The method of claim 2, wherein said construct comprises at least one of a ring model, a coil array with straight line segments model, a polygon model, and a dipole array model.

4. The method of claim 2, further comprising adjusting a model of said volume based on said distortion calculated from said volume.

5. A method comprising:
identifying a distorter volume in a tracking coordinate system;
using at least one computing device to select a model to represent said distorter volume in said tracking coordinate system;
using the at least one computing device to measure a subset of a surface of said distorter volume; and
using the at least one computing device to map a magnetic field generated by said distorter volume using said model and measurements of said subset of said surface, wherein said mapping step further comprises using an integral method and a finite element analysis.

6. The method of claim 5, further comprising adjusting model parameters based on said measurements.

7. The method of claim 5, wherein said model comprises at least one of a ring model, a coil array with straight line segments model, a polygon model, and a dipole array model.

8. The method of claim 5, wherein said magnetic field is mapped based on an approximate set of field sources on a surface of said distorter and adjusted using at least one of an integral method and a finite element analysis.

9. The method of claim 5, further comprising characterizing said tracking coordinate system using a robot.

10. The method of claim 5, further comprising tracking an object using said mapping of said magnetic field.

11. The method of claim 5, wherein said measurements are obtained using a plurality of positions on said surface and one orientation.

12. A system comprising:
a distortion measurement module measuring data from a plurality of mutual inductance sources located on a surface of a volume;
a calculation module calculating distortion from said volume using said plurality of mutual inductance sources using at least one of an integral method and a finite element analysis;
a mapping module mapping a magnetic field around an object, said mapping including effects of said distortion; and
a tracking module tracking said object, said tracking module using said magnetic field mapping to track said object.

13. The system of claim 12, wherein said integral method includes use of a Green's function to calculate distortion.

14. The system of claim 12, wherein said distortion measurement module approximates said volume using a model.

15. The system of claim 14, wherein said model includes at least one of a ring model, a coil array with straight line segments model, a polygon model, and a dipole array model.

16. The system of claim 14, wherein parameters of said model are adjusted based on measurements from said volume.

17. The system of claim 12, wherein said distortion measurement module obtains measurements using a plurality of positions on said surface and one orientation.

18. The system of claim 12, wherein said distortion measurement module measures magnetic fields from said plurality of sources located on said surface of said volume.

* * * * *